United States Patent [19]

Bombardelli et al.

[11] Patent Number: 4,980,475

[45] Date of Patent: Dec. 25, 1990

[54] PROCESS FOR THE PREPARATION OF N-10 ALPHA-METHOXYL-LUMILYSERGOL AND ESTERS, THEREOF, AND INTERMEDIATES FOR THEIR PREPARATION

[75] Inventors: Ezio Bombardelli; Giuseppe Mustich, both of Milan, Italy

[73] Assignee: I d B Holding S.P.A., Milan, Italy

[21] Appl. No.: 716,501

[22] Filed: Mar. 26, 1985

[30] Foreign Application Priority Data

Mar. 27, 1984 [IT] Italy ................. 20242 A/84

[51] Int. Cl.$^5$ ............................................ C07D 457/02
[52] U.S. Cl. ........................................ 546/67; 546/69;
204/157.64; 204/157.71
[58] Field of Search ........................... 546/67, 68, 69;
204/157.64, 157.71

[56] References Cited

U.S. PATENT DOCUMENTS

| | | | |
|---|---|---|---|
| 3,228,943 | 1/1966 | Bernardi et al. | 546/68 |
| 3,647,655 | 3/1972 | Bernardi et al. | 204/157.71 |
| 3,704,233 | 11/1972 | Eich et al. | 546/67 |
| 3,879,554 | 4/1975 | Temperilli et al. | 546/68 |
| 4,232,157 | 11/1980 | Enrico et al. | 546/68 |

FOREIGN PATENT DOCUMENTS 2700276  8/1977  Fed. Rep. of Germany ........ 546/67

OTHER PUBLICATIONS

Barbieri et al., "Ergoline Derivatives-IX....,"*Tetrahedron* 25, (1969), 2401–2405.
Bernardi, Ergoline Derivatives, Chem. Abst. 84:44500b (1975).

*Primary Examiner*—Cecilia Shen
*Attorney, Agent, or Firm*—Browdy and Neimark

[57] ABSTRACT

Processes for the preparation of esters of $N_1$-methyl-$10\alpha$-methoxylumilysergol are described, in which lysergol esters are subjected to N-methylation and subsequently to photochemical reaction with methanol/$H_2SO_4$. The esters of $N_1$-methyl-10-methoxylumilysergol obtained in this way can then be saponified or converted directly into other esters.

7 Claims, No Drawings

PROCESS FOR THE PREPARATION OF N-10 ALPHA-METHOXYL-LUMILYSERGOL AND ESTERS, THEREOF, AND INTERMEDIATES FOR THEIR PREPARATION

The present invention relates to a process for the preparation of $N_1$-methyl-10α-methoxylumilysergol and esters thereof of formula I

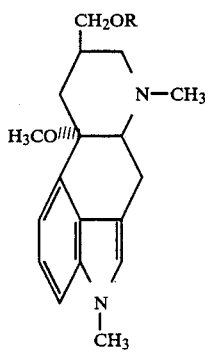

in which R may be hydrogen or an acyl group.

$N_1$-methyl-10α-methoxylumilysergol is a known compound the synthesis of which from lysergol is described, for example, in Italian patent application no. 22011 A/78.

The known process comprises photochemical reaction of lysergol in methanol/sulphuric acid and subsequent methylation at the indole nitrogen of the resulting methoxylumi derivative. The methylation is effected with methyl iodide in the presence of KOH in dimethyl sulphoxide.

In accordance with the known process, yields of 80% in the first stage and 70% in the second have been reported, with a final yield equal to about 56% on the basis of the desired product.

It has been found, moreover, that by operating by the known methods, considerable amounts of the 8-methyl ether and quaternary ammonium salt are formed.

We have now developed a process by which it is possible to obtain the desired product, $N_1$-methyl-10α-methoxylumilysergol, in surprisingly higher total yields equal to about 90%.

Specifically the invention provides a process for the preparation of $N_1$-methyl-10α-methoxylumilysergol and esters thereof of formula I:

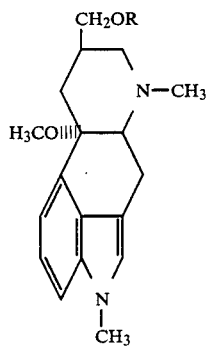

in which R is hydrogen or an ester thereof wherein R is an acyl group characterised in that an ester of $N_1$-methyllysergol is subjected to photochemical reaction with methanol in the presence of sulfuric acid and the resulting ester of $N_1$-methylmethoxylumilysergol is optionally subjected to hydrolysis or transesterification so as to convert the resulting ester to another compound of formula I.

The identity of the acyl group R in the ester of $N_1$-methyllysergol used as starting material is not critical and examples of suitable acyl groups are those of formula R'CO where R' may be an alkyl group, an aralkyl group, an alkaryl group, a p-toluenesulphonyl group or a methane sulphonyl group. The alkyl, aralkyl or alkaryl groups may be unsubstituted or substituted by, e.g. one or more halogen atoms (F, Cl, Br, I). The alkyl groups and the alkyl constituents of the alkaryl and aralkyl groups preferably contain 1-4 carbon atoms (as in etharyl) and the aryl groups are preferably phenyl groups.

The process according to the invention thus in effect consists in the methylation of a lysergol ester followed by photochemical irradiation of the N-methyl derivative. This procedure operates in accordance with the following diagram:

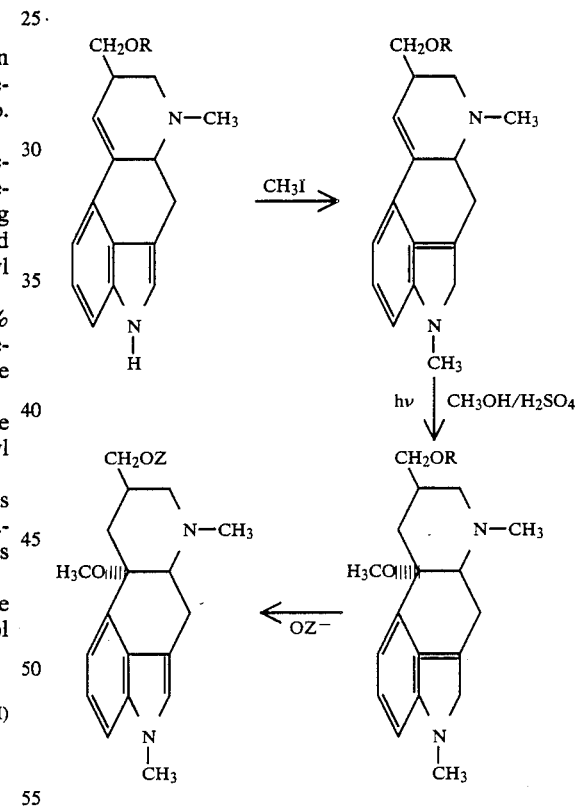

For hydrolysis, $OZ^-$ is hydroxyl, for transesterification $OZ^-$ is acyloxy.

In the foregoing diagram, R represents an acyl radical for example a group R'CO as specified above.

Particularly preferred are acetyl, p-toluenesulphonyl and methanesulphonyl groups.

These acyl groups are good leaving groups and lend themselves to subsequent conversions such as substitutions with carboxylates of formula $RCOO^-$ for obtaining other esters. Thus by reaction with a 5-bromonicotinate salt, nicergolin, a known compound widely used in human therapy, may be obtained.

Lysergol acetate, p-toluenesulphonate and methanesulphonate are novel intermediates and, as such, form further aspects of the present invention.

The sequence of reactions according to the process of the invention does not require isolation of the intermediates, but can be carried out with high yields by a "one pot" method.

The preparation of the starting lysergol esters can be effected by known technique, for example by causing lysergol extracted from natural sources to react with acylating agents, e.g. chlorides or anhydrides of carboxylic or sulphonic acids in pyridine at temperatures between 0° and room temperature. The N-methylation is preferably conducted with methyl iodide in liquid ammonia in the presence of sodium or potassium amide produced in the same reaction medium or in dimethyl sulphoxide containing 0.1% of water and sodium hydride in paraffin suspension.

The photochemical reaction may also be carried out under known conditions, e.g. in methanol and sulphuric acid, normally in methanol containing 5% of concentrated sulphuric acid and at temperatures between $-20°$ and $+10°$ C. The reaction mixture is preferably irradiated with a U.V. source, particularly one having a wave length of from 300 to 370 n.m.

Finally, the optional transesterification of suitable esters of lumilysergol may conveniently be carried out in aprotic solvents such as dimethyl sulphoxide or dimethylformamide with an excess of a salt of, e.g. an aliphatic, aromatic or araliphatic carboxylic acid of which it is desired to obtain the corresponding derivative.

The following Examples illustrate the invention further, without, however, limiting it in any way.

EXAMPLE 1

Preparation of $N_1$-methyl-10α-methoxylumilysergol 0.39 g of metallic potassium and 0.004 g of ferric nitrate are dissolved in 250 ml of liquid ammonia in a multinecked 500 ml flask cooled to $-60°$ C. On complete dissolution, 2.96 g of acetyllysergol and 1.55 g of methyl iodide are added. After two hours, 0.5 g of ammonium chloride is added and the ammonia is distilled off by gradually increasing the temperature. The solid residue is taken up in 400 ml of methyl alcohol to which there are added, with cooling to $-20°$ C., 15 ml of concentrated $H_2SO_4$. The methanol solution containing $N_1$-methyl-8-acetoxylysergol is irradiated with a 500 W immersion UV lamp at 330 nm for about two hours, the course of the reaction being checked by thin-layer chromatography. When transformation is complete, the acid methanol solution is brought to pH 12 with a 30% solution of NaOH in water. Thirty minutes after the change of pH, the solution is diluted with 800 ml of water and immediately extracted with 200 ml of methylene chloride. After counterwashing with water and dewatering over $Na_2SO_4$, the chlorinated solvent is concentrated to dryness under vacuum. 2.85 g of crude $N_1$-methyl-10α-methoxylumilysergol are obtained which, after crystallization from acetone, give 2.705 g of pure product having a melting point of 215°–217° C. M+300.

EXAMPLE 2

Preparation of $N_1$-methyllysergol-8-methanesulphonate

Six grams of lysergol are dissolved in 25 ml of anhydrous pyridine and 3.6 ml of methane sulphonylchloride are added at 0° C. The reaction is complete after about 1 hour; the mixture is diluted with water and the product which precipitates is filtered and washed until there is complete elimination of the pyridine. After drying over night at 50° C., 7.7 g of product are obtained which are dissolved in 100 ml of dimethyl sulphoxide containing 0.1% of water. To this solution there is added with agitation 0.45 g of a 50% suspension of sodium hydride in paraffin washed with hexane. When dissolution is complete, 4 g of methyl iodide in 20 ml of dimethyl sulphoxide are added over a period of about 1 hour. When reaction is complete, the reaction mixture is poured into 400 ml of water and the whole is extracted with ethyl ether (2×300 ml).

After drying over $Na_2SO_4$, the ethereal extracts are concentrated to dryness and the residue is crystallized from ethyl acetate. After drying of the solid at 60° C. over night under vacuum, there is obtained 7.9 g of $N_1$-methyllysergol-8-methanesulphonate having a melting point of 128°–130° C.

EXAMPLE 3

Preparation of lysergol-8-methanesulphonate 10.2 g of lysergol are dissolved in 40 ml of anhydrous pyridine and 7.55 g of methanesulphonic anhydride are added, the temperature being maintained between 0° and 5° C. After 2 hours the solution is poured into 240 ml of cold water; the precipitated product is filtered and thoroughly washed with water to complete elimination of the pyridine. After drying over night under vacuum at 60° C., 13.2 g of the methanesulphonic ester of the alkaloid are obtained with a purity sufficient for the continuation of synthesis. Its characteristics are:

M.p. commencement of decomposition between 170°–180° C.; does not decompose completely until 210° C.

$[\alpha]_2 + 81°$ (c=0.4) in $CHCl_3$.

MS 332 (M+.), 269, 255, 167.

EXAMPLE 4

Preparation of $N_1$-methyllysergol-8-methanesulphonate 0.64 g of K and 0.08 g of ferric nitrate are dissolved in 250 ml of liquid ammonia in a 500 ml flask cooled to $-60°$ C. 3.35 g of lysergol methanesulphonate are added to the solution in small portions. After 30 minutes, 1.25 ml of methyl iodide are added. After 3 hours, 1 g of $NH_4Cl$ is added and the distillation of the ammonia commences. The residue is taken up in water after complete evaporation of the ammonia and the insoluble material is decanted and thorough washing is carried out until the salts are eliminated. After drying, 3.4 g of amorphous $N_1$-methyllysergol-8-methanesulphonate are obtained having the following mass spectrum: 346 (M+.), 331, 251, 237, 181.

EXAMPLE 5

$N_1$-methyl-10α-methoxylumilysergol-8-methanesulphonate 7.9 g of $N_1$-methyllysergol-8-methanesulphonate are dissolved in 160 ml of methanol containing 5 ml of concentrated sulphuric acid. The acid methanol solution is irradiated with a 500 W immersion UV lamp for about two hours, the temperature being maintained at $-20°$ C. (irradiation at 330 nm). When reaction is complete, the methanol solution is diluted with 300 ml of water in the presence of ice, alkalization to pH 7.5 is carried out with NaOH and the water-methanol solution is extracted with methylene chloride. The organic phase is then evaporated to dryness and the residue is crystallized from acetonitrile. 8.1 g of $N_1$-methyl-10α-methoxylumilysergol-8-methanesulphonate having the following characteristics are obtained:

M.p. 119°–120° C.
$[α]_D + 12.2°$ (c=1) in $CHCl_3$.
MS 378 (M+.), 363, 346, 331, 251, 237, 181.

EXAMPLE 6

Preparation of $N_1$-methyl-10α-methoxylumilysergol-8-methanesulphonate 0.64 g of K and 0.08 g of ferric nitrate are dissolved in 250 ml of anhydrous liquid ammonia in a 500 ml flask cooled to −60° C. 2.9 g of 10α-methoxylumilysergol methane sulfonate are added to the solution in small portions. After 30 minutes, 1.25 ml of methyl iodide are added in 30 minutes. After 2 hours, 1 g of ammonium chloride is added and the ammonia is distilled off. The residue is taken up in 50 ml of water and the insoluble solid is filtered. 2.95 g of $N_1$-methyl-10α-methoxylumilysergol-8-methanesulphonate having the following characteristics are obtained:

M.p. 119°–120° C.
$[α]_D + 12.2°$ (c=1) in $CHCl_3$.
MS 378 (M+.) 363, 346, 331, 151, 237, 181.

EXAMPLE 7

Preparation of $N_1$-methyl-10α-methoxylumilysergol 3.8 g of $N_1$-methyl-10α-methoxylumilysergol-8-methanesulphonate are dissolved in a 250 ml flask in 100 ml of tert-butanol containing 1 g of KOH dissolved in 10 ml water. The solution is heated under slight reflux for 7 hours. When reaction has been completed, the tert-butanol is eliminated by distillation and the concentrate is extracted with methylene chloride.

After elimination of the solvent, the residue is crystallized from acetonitrile. 2.7 g of $N_1$-methyl-10α-methoxylumilysergol with m.p. 135°–136° C. are obtained.

EXAMPLE 8

Preparation of $N_1$-methyl-10α-methoxylumilysergol-8-(5′-bromo)-nicotinate 38 g of $N_1$-methyl-10α-methoxylumilysergol-8-methanesulphonate dissolved in 500 ml of dimethylformamide are placed in a multinecked one-liter flask equipped with a stirrer, a thermometer and a condenser.

To this solution, 35 g of sodium 5-bromonicotinate are added in small portions with vigorous agitation and at a temperature of 100° C. From the end of the addition, the reaction is maintained at 100° C. for about 4 hours and then, after cooling, the reaction mixture is poured over 1 kg of crushed ice.

A suspension is obtained which is extracted with methylene chloride. The organic phase is carefully washed with water so as to eliminate the dimethylformamide and then concentration to a low volume is carried out and the residue is crystallized from ethyl ether. 42 g of $N_1$-methyllumilysergol-8-(5′-bromo-nicotinate)-10-methyl ether having the following characteristics are obtained:

M.p. 138°–139° C.;
$[α]^{20}_D = -20.$ (c=1, Py).

We claim:

1. Process for the preparation of $N_1$-methyl-10α-methoxylumilysergol and esters thereof of formula I

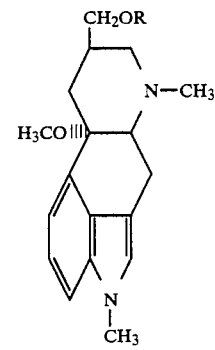

in which OR is selected from the group consisting of hydroxy and esterified hydroxy groups, wherein an ester of $N_1$-methyllysergol is subjected to photochemical reaction with methanol/sulphuric acid to form an ester of $N_1$-methylmethoxylumilysergol and the resulting ester of $N_1$-methylmethoxylumilysergol is optionally subjected to hydrolysis or transesterification.

2. A process according to claim 1 wherein the reaction with methanol and sulphuric acid is carried out while irradiating the reaction mixture with U.V. rays.

3. A process according to claim 2 wherein the U.V. rays have a wavelength in the range from 300 to 370 n.m.

4. A process according to claim 1 wherein OR is selected from the group consisting of (1) an acyloxy group of formula R′COO—wherein R′ is selected from the group consisting of alkyl, aryl, alkaryl or aralkyl groups which are unsubstituted or substituted by one or more halogen atoms, (2) a p-toluenesulphonyloxy, (3) a methanesulphonyoxy and (4) a 5-bromonicotinate group.

5. Process according to claim 1, wherein the ester of $N_1$-methyllysergol of Formula I is selected from the group consisting of acetate, p-toluenesulphonate and methanesulphonate and esters.

6. Process according to claim 1, wherein the starting material is selected from the group consisting of $N_1$-methyllysergol p-toluenesulphonate and methanesulphonate.

7. Process according to claim 1 for the preparation of nicergolin, wherein said ester of $N_1$-methyllysergol is $N_1$-methyllysergol 5-bromonicotinate.

* * * * *